(12) United States Patent
Lindsey et al.

(10) Patent No.: US 8,142,661 B2
(45) Date of Patent: Mar. 27, 2012

(54) RESIDUAL STREAM UPGRADING IN A PROPYLENE OXIDE-STYRENE MONOMER PROCESS

(75) Inventors: Dan D. Lindsey, Houston, TX (US); Karl P. Rufener, Drexel Hill, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 558 days.

(21) Appl. No.: 12/286,229

(22) Filed: Sep. 29, 2008

(65) Prior Publication Data

US 2010/0078391 A1    Apr. 1, 2010

(51) Int. Cl.
*B01D 11/00* (2006.01)
*C07C 7/10* (2006.01)

(52) U.S. Cl. ............ 210/639; 203/39; 203/89; 210/774; 210/749; 210/806; 95/258; 585/833; 585/858; 585/867; 585/435; 585/500

(58) Field of Classification Search ............. 210/634, 210/638, 639, 774, 806, 739, 800; 585/833, 585/858, 864–867, 435–437, 500; 203/28, 203/39, 89; 95/258, 241
See application file for complete search history.

(56) References Cited

U.S. PATENT DOCUMENTS

| | | | |
|---|---|---|---|
| 3,351,635 A | | 11/1967 | Kollar |
| 3,439,001 A | | 4/1969 | Pell et al. |
| 4,039,602 A | * | 8/1977 | Uitti .............................. 585/441 |
| 4,066,706 A | | 1/1978 | Schmidt |
| 4,221,659 A | * | 9/1980 | Harris et al. .................. 210/639 |
| 4,262,143 A | | 4/1981 | Becker |
| 5,210,354 A | | 5/1993 | Dubner et al. |
| 5,276,235 A | | 1/1994 | Dubner |
| 5,675,055 A | * | 10/1997 | Evans et al. ................... 585/858 |
| 6,080,894 A | * | 6/2000 | Oyague et al. ................ 568/700 |
| 6,712,882 B1 | * | 3/2004 | De Bie et al. .................. 95/245 |
| 2005/0234284 A1 | * | 10/2005 | Escrig et al. .................. 585/866 |

FOREIGN PATENT DOCUMENTS

| | | |
|---|---|---|
| EP | 0767171 A | 4/1997 |
| EP | 0943611 A | 9/1999 |
| EP | 1586568 A | 10/2005 |

* cited by examiner

*Primary Examiner* — Joseph Drodge

(57) ABSTRACT

In the co-production of propylene oxide and styrene monomer, there is produced a sodium-containing heavy residue stream previously suitable only as a low grade fuel. In accordance with the invention, the heavy residue stream is mixed with a hydrocarbon and an aqueous acid, and the resulting mixture is separated into an aqueous sodium salt-containing slurry phase and an organic phase reduced in sodium.

11 Claims, No Drawings

RESIDUAL STREAM UPGRADING IN A PROPYLENE OXIDE-STYRENE MONOMER PROCESS

FIELD OF THE INVENTION

The present invention relates to the improved acid treatment of heavy residual process streams formed in the co-production of propylene oxide and styrene monomer.

BACKGROUND OF THE INVENTION

The co-production of propylene oxide and styrene monomer (the "POSM process") involves the oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to produce styrene monomer. The basic patent describing this process is U.S. Pat. No. 3,351,635.

In the POSM process, various distillation steps are employed in order to separate unreacted reagents as well as various product streams, and generally one or more caustic treatment steps are employed in order to reduce the acidic characteristics of various streams. From the process, a heavy residue stream containing relatively high levels of sodium compounds is formed. Left untreated, the heavy residue is a low value product stream suitable only for use as a low grade fuel.

U.S. Pat. No. 5,210,354 discloses a process to upgrade the low value heavy residue and recover valuable products. The process involves treating the low value stream with aqueous acid, then phase separating the resulting mixture into an aqueous phase containing most of the sodium previously associated with the low value stream and an organic stream phase having reduced sodium content. The resulting organic stream phase can be directly cracked at elevated temperature with the formation of 1-phenyl ethanol and styrene or the organic stream phase can be passed to a wiped film evaporator where a volatile stream is separated and cracked to form 1-phenyl ethanol and styrene, the heavy stream from the evaporator comprising a useful fuel.

U.S. Pat. No. 5,276,235 discloses a process wherein the sodium-containing heavy residue formed in the POSM process is mixed with acid having a molar concentration with respect to water above that which corresponds to the product salt solubility limit. The resulting admixture is phase separated into an aqueous sodium salt-containing slurry phase and an organic phase having reduced sodium content.

In the prior art phase separation processes, it is found that large volumes of a rag layer tend to form in the separator vessels. The rag layer is an emulsion of water in the heavy organic layer that does not separate into either an organic or an aqueous phase. The rag layer prevents complete separation of the aqueous and organic phases, and reduces the efficiency of the separation process.

In sum, new and improved processes to upgrade the low value heavy residue produced in POSM process are needed.

SUMMARY OF THE INVENTION

A process is provided whereby sodium is removed from a heavy residue formed in the co-production of propylene oxide and styrene. The process of the invention involves adding a hydrocarbon and an aqueous acid to the heavy residue, and separating the resulting mixture into an aqueous sodium salt-containing phase and an organic phase having reduced sodium content. The process of the invention reduces or eliminates the formation of a rag layer in the separation process, and improves the removal of sodium from the organic phase.

DETAILED DESCRIPTION OF THE INVENTION

The process of the invention comprises reducing sodium content in a heavy residue formed in the POSM process for the co-production of propylene oxide and styrene. The POSM process is well known in the art.

In the POSM process, ethyl benzene is first reacted with molecular oxygen at elevated temperature in accordance with known techniques to form ethyl benzene hydroperoxide. U.S. Pat. No. 4,066,706 provides a comprehensive description of this reaction. Suitably, a small amount of alkali is incorporated in the oxidation mixture in order to improve oxidation rate and selectivity, as described in U.S. Pat. No. 4,262,143.

Ethyl benzene hydroperoxide is then reacted with propylene to form propylene oxide and 1-phenyl ethanol. U.S. Pat. No. 3,351,635 describes suitable conditions and catalysts for this reaction.

The epoxidation reaction mixture is generally caustic washed and subjected to a series of distillations in order to separate materials contained therein. Generally, the reaction mixture is first distilled to separate unreacted propylene overhead from heavier components. The separated propylene is conveniently recycled to the epoxidation step.

The heavier components are then further distilled after caustic wash in a series of distillations to separate product propylene oxide, product 1-phenyl ethanol, and unreacted ethyl benzene which can be recycled, preferably after a caustic wash as described in U.S. Pat. No. 3,439,001. The 1-phenyl ethanol stream is dehydrated to product styrene monomer in accordance with known procedures such as described in U.S. Pat. No. 3,351,635.

The separation processes leave a heavy organic sodium-containing low value product stream.

In accordance with the present invention, the sodium-containing heavy residue is treated in order to upgrade the stream and to optionally recover valuable products therefrom.

The upgrade process comprises adding a hydrocarbon and an aqueous acid to the heavy residue, and phase separating the resulting mixture into an aqueous sodium-containing phase and an organic phase having reduced sodium content.

The hydrocarbon is preferably a $C_5$-$C_{12}$ hydrocarbon, more preferably $C_5$-$C_{12}$ alkane or a $C_6$-$C_{12}$ aromatic. Preferably, the hydrocarbon comprises ethyl benzene or hexane. The hexane may be n-hexane, a branched hexane, or a mixture of hexanes. The amount of hydrocarbon is preferably at least 5 percent by weight, and more preferably between 10 and 40 percent by weight, of the total amount of heavy residue.

The aqueous acid employed in the heavy organic treatment is an aqueous solution of an acid, preferably a mineral acid or a carboxylic acid. Preferred mineral acids include sulfuric acid, hydrochloric acid, phosphoric acid, nitric acid, and the like, and mixtures thereof. Carboxylic acid compounds contain one or more carboxylic acid functionalities. Examples of carboxylic acids include, but are not limited to, oxalic acid, acetic acid, pyruvic acid, lactic acid, and the like, and mixtures thereof. Sulfuric acid, phosphoric acid, oxalic acid, and mixtures thereof are especially preferred. Sulfuric acid is most preferred.

The acid is preferably used in at least an amount sufficient to react with all of the sodium in the heavy organic stream, that is, the amount of aqueous acid used is such that the ratio of $H^+$ ions to $Na^+$ ions is preferably at least 1/1. In the case of sulfuric acid, sufficient acid is preferably used to form sodium sulfate, i.e. 0.5 mole of sulfuric acid per mole of contained sodium, and more preferably at least 1 mole sulfuric acid per mole of sodium are employed sufficient to form sodium bisulfate. Where other acids are used, equivalent amounts are employed. It is preferable that the amount of aqueous acid used is sufficient to keep the evolved sodium salt in solution. The higher the $H^+$ ratio the more sodium is removed. The concentration of the aqueous acid used is preferably between 10 and 96% weight percent, with 15 to 40% weight percent more preferred.

Optionally, water may be added along with the aqueous acid and hydrocarbon to aid in the phase separation process.

Preferably, the heavy residue is thoroughly mixed with the hydrocarbon and aqueous acid prior to the separation step. The hydrocarbon and aqueous acid may be added simultaneously or can be added separately to the heavy residue. The order of addition of the hydrocarbon and aqueous acid are not critical. If performed, the mixing is accomplished at relatively mild conditions, preferably 20° C. to 100° C., and more preferably 40° C. to 90° C. The hydrocarbon and/or aqueous acid can also be added directly into the separation vessel along with the heavy residue.

The resulting mixture is separated into immiscible phases, specifically an aqueous sodium-containing phase and an organic phase having reduced sodium content. The separation is preferably performed by gravity-driven phase separation such as decantation. In decantation, the mixed aqueous acid/hydrocarbon/heavy residue stream is introduced into a decanter unit where phase separation takes place. Gravity-driven phase separation results in an aqueous sodium salt-containing phase and an organic phase having reduced sodium content.

The separation is operated under conditions which are effective to provide an immiscible aqueous sodium-containing phase and an organic phase having reduced sodium content. Preferably, the aqueous sodium-containing phase contains at most negligible amounts (i.e., less than 2 weight percent) of organic compounds. For decantation, the volume of the decanter should be sufficient to provide a suitable residence time for phase separation to occur at a specified flow rate. The temperature in the phase separation will preferably be between about 20° C. to 85° C., and more preferably between about 25° C. to 70° C.

The organic phase having reduced sodium content may be used as an upgraded fuel stream without further processing. Preferably, the organic phase having reduced sodium content is further processed to separate the hydrocarbon out of the organic phase. The hydrocarbon separation is preferably performed by distillation. The distillation is preferably a low temperature, vacuum distillation to avoid or reduce the possible generation of styrene in the organic phase. Preferably, the organic phase having reduced sodium content is distilled to produce an overhead stream comprising hydrocarbon and a bottoms stream comprising heavy organic components formed in the POSM process. The resulting overhead stream comprising hydrocarbon is preferably recycled back to the addition step for further addition to the heavy residue and aqueous acid.

Optionally, at least a portion of the organic phase having reduced sodium content (or the bottoms stream following hydrocarbon removal) is further upgraded by cracking to produce styrene monomer. In one practice, a compatible acid catalyst such as p-toluene sulfonic acid is preferably added to the organic phase or bottoms stream, and the resulting mixture is cracked at elevated temperature to form 1-phenyl ethanol and styrene monomer. The 1-phenyl ethanol and styrene monomer are preferably separated by distillation from remaining heavy materials. Conditions for the cracking include temperatures of 70° C. to 300° C., preferably 120° C. to 220° C. and pressures below atmospheric, e.g. 100 to 400 mm Hg which are appropriate for vaporization of light materials.

In another, more preferred practice, at least a portion of the organic phase or bottoms stream is subjected to a wiped film evaporation in order to separate a portion of the stream as volatile overhead fraction. This overhead fraction can be cracked at elevated temperatures as described above to produce styrene monomer. Optionally, the volatile overhead stream can be passed directly to the 1-phenyl ethanol dehydration step employed in commercial POSM processes wherein components of the volatile overhead are converted to styrene monomer at the conditions conventionally employed for the 1-phenyl ethanol dehydration.

Product 1-phenyl ethanol and styrene monomer from the further optional upgrade represent increased yields of desired products of the overall process. Also, the heavy materials from the optional upgrade are useful as an upgraded fuel by virtue of the low sodium content.

The following examples merely illustrate the invention. Those skilled in the art will recognize many variations that are within the spirit of the invention and scope of the claims.

COMPARATIVE EXAMPLE 1

Batch Separation with No Added Hydrocarbon

A heavy organic residue stream from the propylene oxide-styrene monomer process (200 g, produced as described in U.S. Pat. No. 5,210,354, primarily comprised of oxygenated aryl compounds with molecular weights greater than 225 g/mol and containing about 1.0 wt. % sodium) is introduced to a batch vessel, heated to 60° C. and then mechanically agitated under atmospheric pressure. Aqueous sulfuric acid (32 g, of 20 wt. % $H_2SO_4$) is added and the material is agitated for 1 hour. The mixture is moved to a jacketed separation vessel, which is also heated to 60° C., and is allowed to separate under gravity. Normal separation times are 24-48 hours for full phase separation. Sodium salts and ash are preferentially solubilized in the aqueous phase and formed rag layer. The upgraded fuel is decanted from the aqueous phase and rag layer. The sodium level in the upgraded fuel is typically less than 100 ppm.

EXAMPLE 2

Batch Separation with Added Ethyl Benzene

EXAMPLE 2A

Comparative Example 1 is repeated, with the exception that 20 g of ethyl benzene is added to 180 g of heavy organic residue stream before mixing. No stable rag layer is formed in this case. The sodium and ash is still preferentially dissolved in the aqueous phase. Compared to Comparative Example 1, separation time is reduced by about a factor of 4, to 6-12 hours for full separation. The ethyl benzene solvent can later be recovered via distillation or other separation techniques, or can remain with the fuel. Sodium level in this upgraded fuel is typically less than 50 ppm.

EXAMPLE 2B

Example 2A is repeated, with the exception that 20 g of ethyl benzene is added directly to the mixing vessel during agitation instead of to the heavy organic residue stream before mixing. The separation time and sodium and ash removal are similar to Example 2A. Sodium level in this upgraded fuel is typically less than 50 ppm.

EXAMPLE 3

Batch Separation with Added Hexanes

EXAMPLE 3A

Example 2A is repeated, with the exception that 20 g of mixed hexanes are added during agitation in place of ethyl benzene. Mixed hexanes include, but may not be limited to, n-hexane, cyclohexane, 2-methylpentane, and 3-methylpentane. The separation time and sodium and ash removal are similar to Example 2A. A separate, hexane-rich, organic layer may form. This layer can remain with the upgraded fuel and does not typically need further separation. However, the hexanes can be separated through normal separation techniques. Sodium level in this upgraded fuel is typically less than 50 ppm.

EXAMPLE 3B

Example 2B is repeated, with the exception that 20 g of mixed hexanes is added directly to the mixing vessel during agitation instead of to the heavy organic residue stream before mixing. The separation time and sodium and ash removal are similar to Example 2B. Sodium level in this upgraded fuel is typically less than 50 ppm.

COMPARATIVE EXAMPLE 4

Continuous Separation with No Added Hydrocarbon

A continuous feed of heavy organic residue is fed into a continuously agitated vessel held at 60° C. and under atmospheric pressure. A proportional amount of 20% aqueous sulfuric acid is added to this same tank. Feed rates on the small scale are typically 0.41 g/min 20% aqueous sulfuric acid, 2.31 g/min organic residue, but can be scaled up directly for larger volumes. The material is combined during agitation and is held for a one-hour residence time. A stream of this material is continuously moved to a continuous decanting vessel. The decanting vessel can be held at 60° C. or at ambient temperature. The materials are allowed to separate under gravity. The material is removed from the decanting vessel at a rate so as to maintain a one hour residence time, after initial filling. Upgraded organic fuel is removed from the top phase and sodium-rich aqueous phase is removed from the bottom. A rag layer is noted to form and increases with time, eventually filling the decanting vessel. Sodium level in this upgraded fuel is typically less than 250 ppm.

EXAMPLE 5

Continuous Separation with Ethyl Benzene

Comparative Example 4 is repeated, with the exception that an additional 0.46 g/min ethyl benzene flow is added directly into the mixing vessel. A rag layer does not accumulate. Decanting vessel residence time is one hour after initial filling. Separation of the aqueous and fuel phases is visually observed earlier than that of Comparative Example 4. Sodium level in this upgraded fuel is typically less than 50 ppm.

The results show that acid treatment of a heavy residual POSM process stream is improved by use of added hydrocarbon, which reduces or eliminates the formation of rag layer and leads to improved separation of sodium from the organic phase.

We claim:

1. A process for removing sodium from a heavy residue formed in the co-production of propylene oxide and styrene, said process comprising adding a hydrocarbon comprising hexane and an aqueous acid to the heavy residue, and separating the resulting mixture into an aqueous sodium salt-containing phase and an organic phase having reduced sodium content.

2. The process of claim 1 wherein the hydrocarbon comprises ethyl benzene.

3. The process of claim 1 wherein the hydrocarbon is used in an amount between 10 and 40 percent by weight, based on the total amount of heavy residue.

4. The process of claim 1 wherein the aqueous acid comprises an acid selected from the group consisting of sulfuric acid, phosphoric acid, oxalic acid, and mixtures thereof.

5. The process of claim 4 wherein the acid is sulfuric acid.

6. The process of claim 1 wherein the phase separation is conducted at a temperature in the range of 25° C. to 70° C.

7. The process of claim 1 wherein at least a portion of the organic phase is cracked to form styrene monomer.

8. The process of claim 7 wherein the organic phase is subjected to wiped film evaporation to produce a volatile stream, and the volatile stream is cracked to form styrene monomer.

9. The process of claim 1 wherein the organic phase is distilled to produce an overhead stream comprising the hydrocarbon.

10. The process of claim 9 wherein at least a portion of the overhead stream is cracked to form styrene monomer.

11. The process of claim 10 wherein the overhead stream is subjected to wiped film evaporation to produce a volatile stream, and the volatile stream is cracked to form styrene monomer.

\* \* \* \* \*